US012673222B2

(12) United States Patent
Dalfsen et al.

(10) Patent No.: US 12,673,222 B2
(45) Date of Patent: Jul. 7, 2026

(54) COMPOSITE FIELD SEQUENCING (CFS) FOR PROTON BEAM THERAPY

(71) Applicant: Elekta, Inc., Atlanta, GA (US)

(72) Inventors: Raymond Philip Dalfsen, Adelaide (AU); Louis Arunus Genet, Newcastle (AU)

(73) Assignee: Elekta, Inc., Atlanta, GA (US)

( * ) Notice: Subject to any disclaimer, the term of this patent is extended or adjusted under 35 U.S.C. 154(b) by 824 days.

(21) Appl. No.: 17/662,227

(22) Filed: May 5, 2022

(65) Prior Publication Data

US 2023/0356004 A1    Nov. 9, 2023

(51) Int. Cl.
*A61N 5/10* (2006.01)
*G16H 20/40* (2018.01)
*G16H 30/40* (2018.01)

(52) U.S. Cl.
CPC ........... *A61N 5/1071* (2013.01); *A61N 5/103* (2013.01); *G16H 20/40* (2018.01); *G16H 30/40* (2018.01); *A61N 5/1045* (2013.01); *A61N 2005/1087* (2013.01)

(58) Field of Classification Search
CPC .......... A61N 5/1071; A61N 2005/1087; A61N 5/103; A61N 5/1045; A61N 5/1047; A61N 5/1031; G16H 20/40; G16H 30/40; G16H 40/60
See application file for complete search history.

(56) References Cited

U.S. PATENT DOCUMENTS

2013/0086500 A1* 4/2013 Kane ..................... A61N 5/1079
715/771
2018/0078789 A1* 3/2018 Ollila ................... A61N 5/1042
2021/0138268 A1* 5/2021 Yan ........................ G16H 20/40

FOREIGN PATENT DOCUMENTS

KR      20100119106      11/2010

OTHER PUBLICATIONS

"European Application Serial No. 23157757.8, Extended European Search Report mailed Jan. 17, 2024", 8 pgs.
Jianguo, Qian, "Dose reconstruction for volumetric modulated arc therapy (VMAT) using cone-beam CT and dynamic log files This work was presented at the 2009 Annual Meeting of AAPM, Anaheim, CA.; VMAT dose reconstruction", Physics in Medicine and Biology, Institute of Physics Publishing, Bristol GB, vol. 55, No. 13, (Jul. 7, 2010), 3597-3610.
"European Application Serial No. 23157757.8, Response filed Aug. 14, 2024 to Extended European Search Report mailed Jan. 17, 2024", 14 pgs.
"European Application Serial No. 23157757.8, Communication Pursuant to Article 943 EPC mailed Oct. 6, 2025", 4 pgs.

* cited by examiner

*Primary Examiner* — Robert H Kim

(74) *Attorney, Agent, or Firm* — Schwegman Lundberg & Woessner, P.A.

(57)      ABSTRACT

System and techniques may be adapted for use in composite field sequencing for proton therapy. A technique may include generating a proton therapy plan in a treatment planning system, the proton therapy plan including a plurality of static fields. The technique may include creating a single data file of a single dynamic field representing the plurality of static fields. The single data file may be sent to a proton therapy system for delivery of the single dynamic field. The technique may include receiving a response information related to a dose delivered to a patient by the single dynamic field.

24 Claims, 11 Drawing Sheets

MAGNETIC SCANNER

RANGE SHIFTER PLATE

PROTON PENCIL BEAM

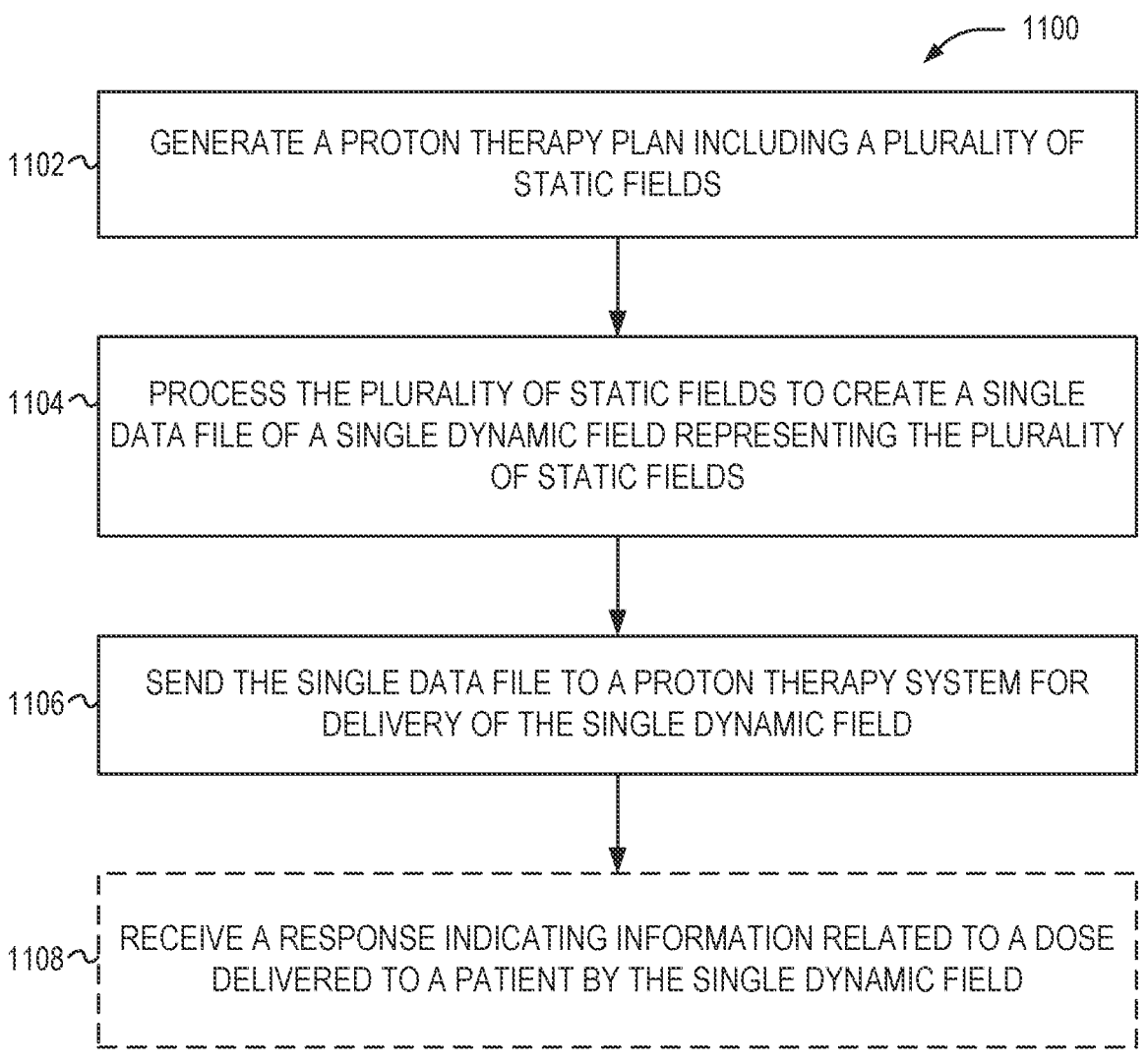

1100

1102 — GENERATE A PROTON THERAPY PLAN INCLUDING A PLURALITY OF STATIC FIELDS

1104 — PROCESS THE PLURALITY OF STATIC FIELDS TO CREATE A SINGLE DATA FILE OF A SINGLE DYNAMIC FIELD REPRESENTING THE PLURALITY OF STATIC FIELDS

1106 — SEND THE SINGLE DATA FILE TO A PROTON THERAPY SYSTEM FOR DELIVERY OF THE SINGLE DYNAMIC FIELD

1108 — RECEIVE A RESPONSE INDICATING INFORMATION RELATED TO A DOSE DELIVERED TO A PATIENT BY THE SINGLE DYNAMIC FIELD

FIG. 11

COMPOSITE FIELD SEQUENCING (CFS) FOR PROTON BEAM THERAPY

BACKGROUND

Radiation therapy or "radiotherapy" may be used to treat cancers or other ailments in mammalian (e.g., human and animal) tissue. One such radiotherapy technique is referred to as "gamma knife," by which a patient is irradiated using a number of lower-intensity gamma rays that converge with higher intensity and high precision at a targeted region (e.g., a tumor). In another example, radiotherapy is provided using a linear accelerator ("linac"), whereby a targeted region is irradiated by high-energy particles (e.g., electrons, high-energy photons, and the like). In another example, radiotherapy is provided using a heavy charged particle accelerator (e.g., protons, carbon ions, and the like). The placement and dose of the radiation beam is accurately controlled to provide a prescribed dose of radiation to the targeted region. The radiation beam is also generally controlled to reduce or minimize damage to surrounding healthy tissue, such as may be referred to as "organ(s) at risk" (OARs). Radiation may be referred to as "prescribed" because generally a physician orders a predefined dose of radiation to be delivered to a targeted region such as a tumor.

BRIEF DESCRIPTION OF THE DRAWINGS

FIG. 11 illustrates a flowchart showing a technique for composite field sequencing for proton therapy, in accordance with an embodiment.

Figure 1:
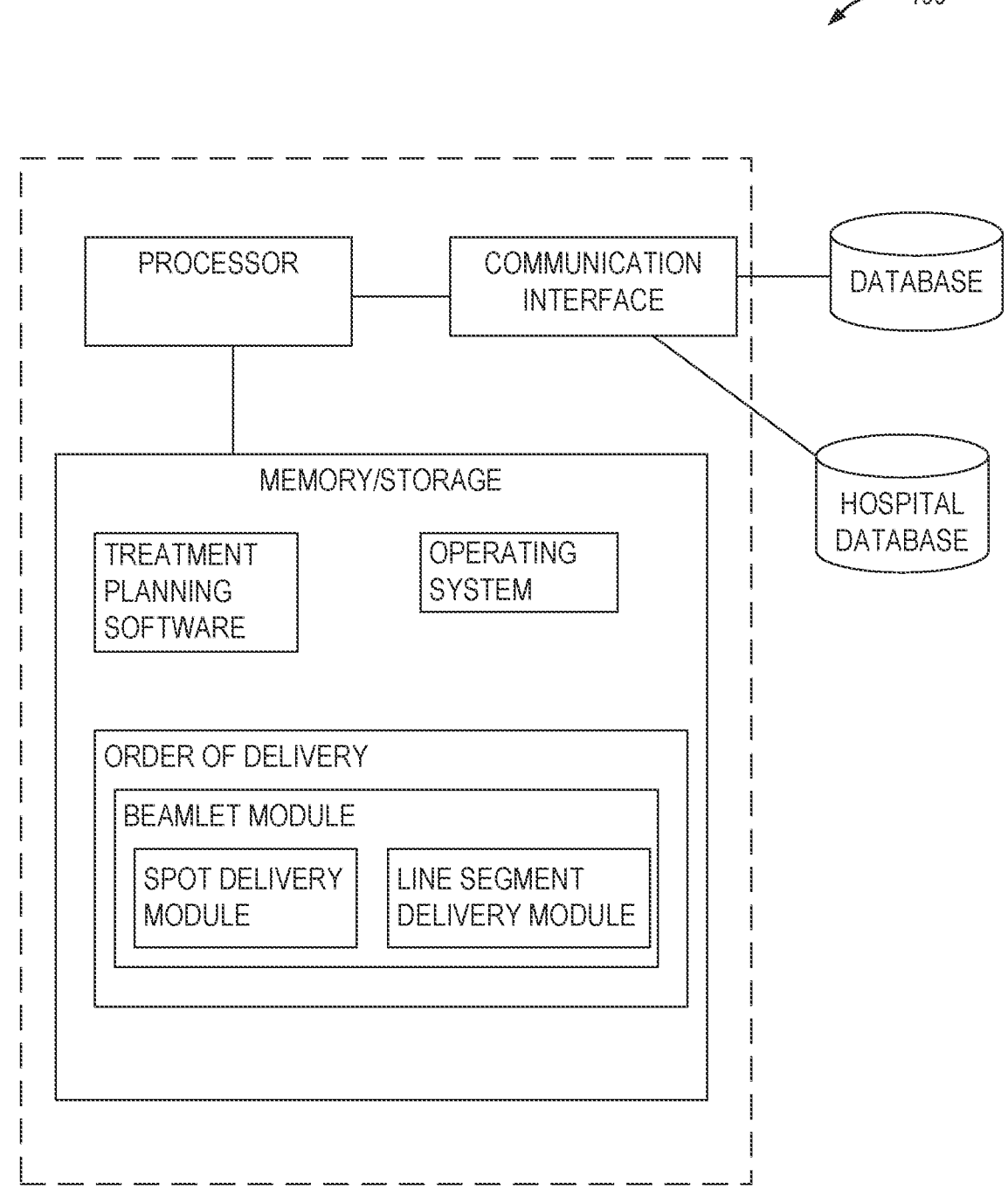
FIG. 1 illustrates generally an example of a system, such as may include a particle therapy system controller, in accordance with an embodiment.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As discussed above, radiation therapy or "radiotherapy" is used to treat cancers or other ailments in mammalian (e.g., human and animal) tissue. Generally, ionizing radiation in the form of a collimated beam is directed from an external radiation source toward a patient. Modulation of a radiation beam may be provided by one or more attenuators or collimators (e.g., a multi-leaf collimator). The intensity and shape of the radiation beam may be adjusted by collimation avoid damaging healthy tissue (e.g., OARs) adjacent to the targeted tissue by conforming the projected beam to a profile of the targeted tissue.

In one approach, radiation therapy may be provided by using particles, such as protons, instead of electrons. This typically may be referred to as proton therapy. One significant known advantage of proton therapy is it provides superior dose distribution with minimal exit dose compared to other forms of radiation therapy, such as x-ray therapy. There is a significant reduction of dose to organs at risk (OAR) because of the minimal exit dose. Further advantages include lower dose per treatment, which lowers the risk of side effects and may improve quality of life during and after proton therapy treatment.

FIG. 1 illustrates generally an example of a system 100, such as may include a particle therapy system controller, in accordance with an embodiment. The system 100 may include a database or a hospital database. The particle therapy system controller may include a processor, communication interface, or memory. The memory may include treatment planning software, an operating system, or a delivery controller. The delivery controller may include a beamlet module for determining or planning spot delivery (e.g., using a spot delivery module) or line segment delivery (e.g., using a line segment delivery module).

In an example, the spot delivery module or the beamlet module may be configured to plan size of beamlets, location of a target or spot, or the like. The beamlet module may be used to determine an order of delivery of beamlets, for example in a spiral pattern as described herein. The order of delivery module may be in communication with the treatment planning software for planning delivery of beamlets. For example, the treatment planning software may be used to determine or plan gantry angle, gantry speed, beamlet size, spiral pattern (e.g., clockwise or counterclockwise), angle range fora particular spiral pattern (e.g., every ten degrees of the gantry rotation), or the like.

The processor may implement the plan, such as by communicating, via the communication interface or otherwise, to components used to implement the plan (e.g., to control devices or components, such as those described below with reference to FIG. 3). In an example, the communication interface may be used to retrieve stored information from a database or a hospital database (e.g., patient information, past procedure information for the patient or other patients, procedure instructions, information about particular devices or components, or the like).

Figure 2:
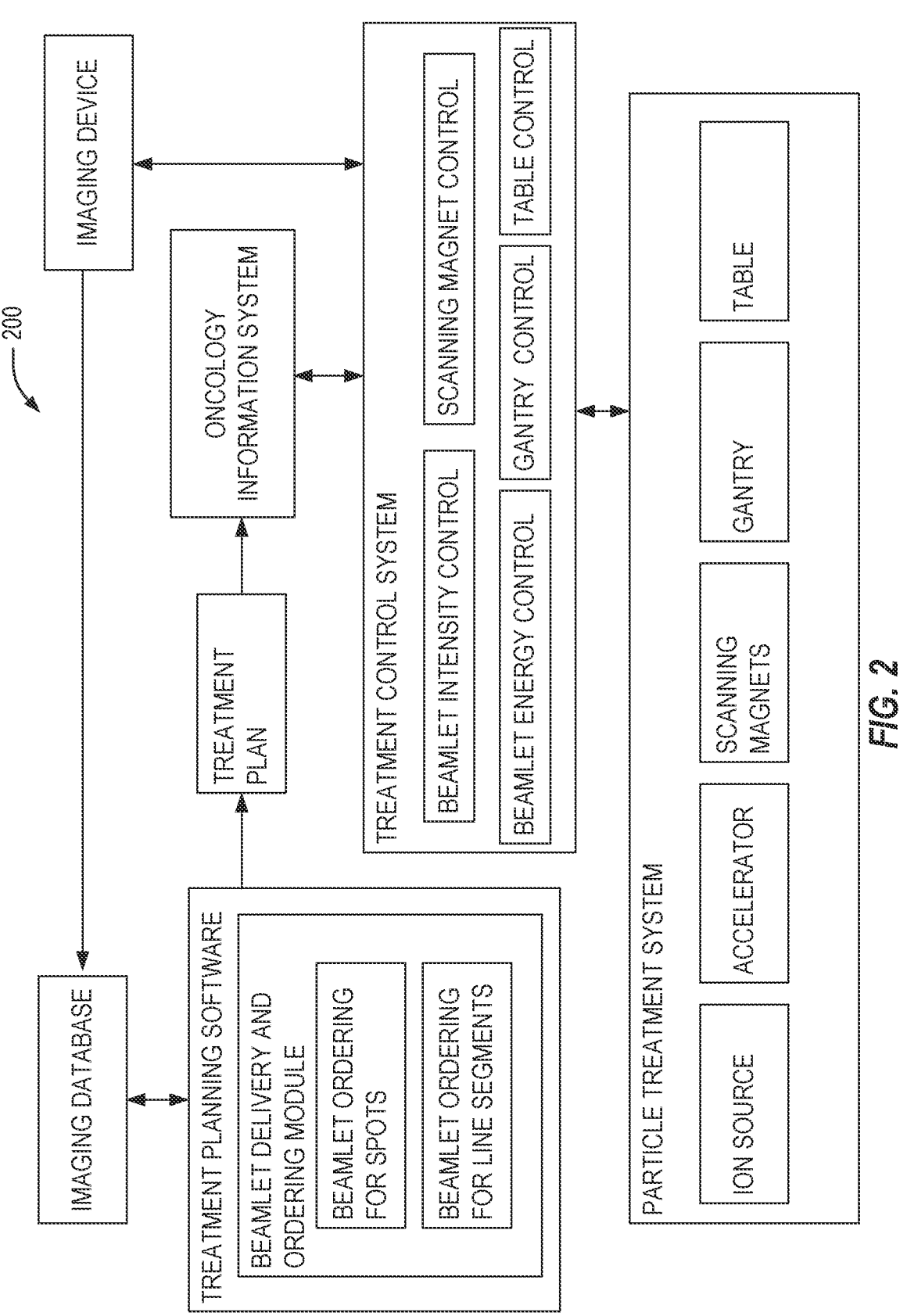
FIG. 2 illustrates generally an example of a radiation therapy system, such as may include a particle treatment system and an imaging acquisition device, in accordance with an embodiment.

FIG. 2 illustrates generally an example of a radiation therapy system 200, such as may include a particle treatment system and an imaging acquisition device, in accordance with an embodiment. The particle treatment system includes an ion source, an accelerator, and scanning magnets, each of which is described in more detail below with respect to FIG.

3. The particle treatment system includes a gantry and a table, where the gantry may be mounted on the table, affixed to the table, or stabilized with respect to the table. The table may hold a patient. The gantry may be a rotating gantry, and may rotate with respect to the table (e.g., around the table) or with respect to the patient (and the table or a portion of the table may rotate with the gantry).

The particle treatment system may communicate with a treatment control system, which may be used to control actions of the particle treatment system. The treatment control system may communicate with an imaging acquisition device (e.g., to receive images taken by the imaging acquisition device or an imaging database) or an oncology information system. The oncology information system may provide treatment plan details to the treatment control system, such as received from treatment planning system. The treatment control system may use the treatment plan to control the particle treatment system (e.g., activate the gantry, the ion source, the accelerator, the scanning magnets, a particle beam, or the like). The treatment control system, for example, may include a beamlet intensity control, a beamlet energy control, a scanning magnet control, a table control, a gantry control, etc. In an example, the beamlet intensity control and the beamlet energy control may be used to activate a beamlet of a particular size or to target a particular location. The scanning magnetic control may be used to deliver beamlets according to the treatment plan, for example in a spiral pattern. The gantry control or the table control may be used to rotate the gantry.

The treatment planning software may include components such as a beamlet delivery and ordering module, with, for example, separate controls for beamlet ordering for spots or line segments. The treatment planning software is described in more detail above with respect to FIG. 1. The treatment planning software may access an imaging database to retrieve images or store information. When a treatment plan is completed, the treatment planning software may send the plan to an oncology information system for communication with the treatment control system.

Figure 3:
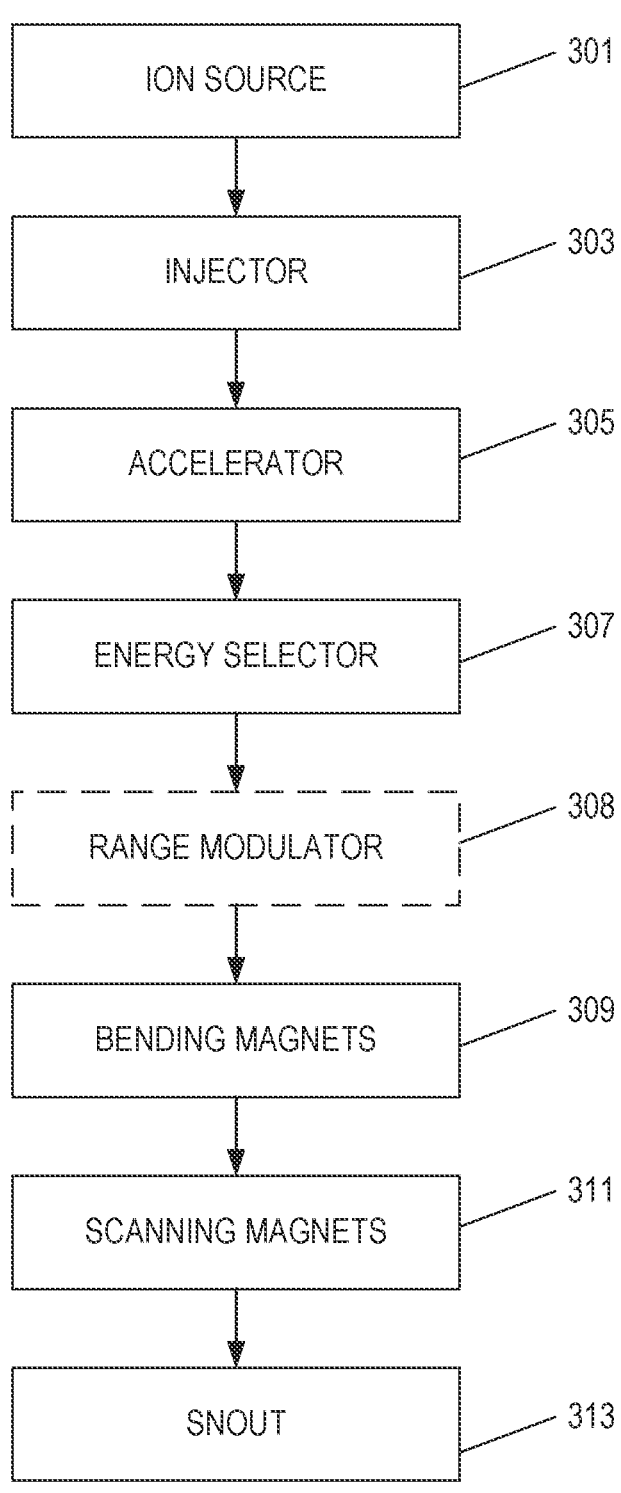
FIG. 3 illustrates generally a particle treatment system that may include a radiation therapy output configured to provide a proton therapy beam, in accordance with an embodiment.

FIG. 3 illustrates in an embodiment of a particle treatment system 300 that may include a radiation therapy output configured to provide a proton therapy beam. The particle treatment system 300 includes an ion source 301, an injector 303, an accelerator 305, an energy selector 307, a plurality of bending magnets 309, a plurality of scanning magnets 311, and a snout 313.

The ion source 301, such as a synchrotron (not shown) may be configured to provide a stream of particles, such as protons. The stream of particles is transported to an injector 303 that provides the charged particles with an initial acceleration using a Coulomb force. The particles are further accelerated by the accelerator 305 to about 10% of the speed of light. The acceleration provides energy to the particles, which determines the depth within tissue the particles may travel. The energy selector 307 (e.g., a range scatter) may be used to select the energies of the protons to be delivered to the patient. In an embodiment called passive scattering, an optional range modulator 308 (e.g., also called a ridge filter or a range modulation wheel) may be utilized to broaden the beam to fit the tumor. After selecting energies, a set of bending magnets 309 may be utilized to transport the stream of protons into a radiation therapy treatment room of a hospital. Further, scanning magnets 311 (e.g., x-y magnets) are used to spread the proton beam to, or trace, an exact image of the tumor shape. A snout 313 is used to further shape the proton beam. In various embodiments, the stream of particles may be composed of carbon ions, pions, or positively charged ions.

Figure 4:
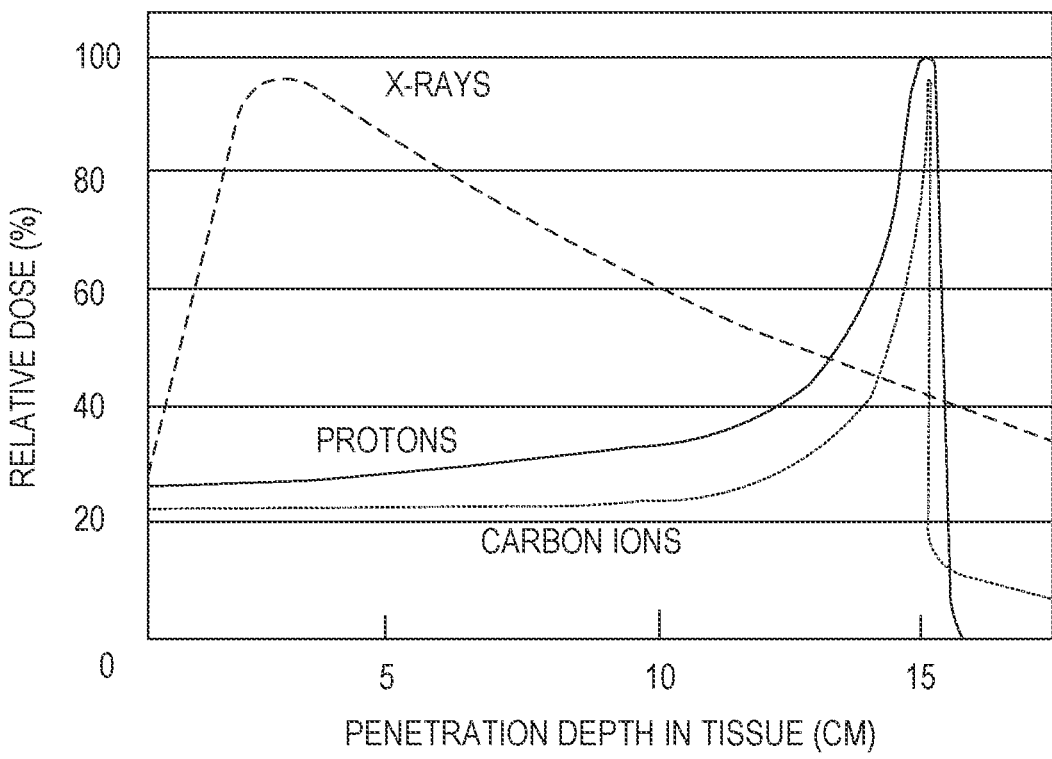
FIG. 4 illustrates generally radiation dose depths in human tissue for various types of particles, in accordance with an embodiment.

FIG. 4 provides an illustration of a comparison of radiation dose depths for various types of particles in human tissue. As shown, the relative depth of penetration into human tissue of photons (e.g., x-rays) versus protons versus carbon ions is provided (e.g., including any radiation dose provided at a distance beneath the surface, including secondary radiation or scatter). Each radiation dose is shown relative to the peak dose for a proton beam having a single energy which has been set to 100%.

The mono-energetic (e.g., single energy) proton beam indicates a plateau region starting at approximately 25% that gradually increases until approximately 10 cm depth in tissue where it rapidly increases to the Bragg Peak at 15 cm and then advantageously falls to zero within a short distance. No additional dose is delivered at the end of the Bragg peak.

The photon beam (e.g., labelled as X-rays) indicates the initial build up due to electron scatter (e.g., the primary means by which X-rays deliver dose to tissue is through transfer of energy to electrons in the tissue), This is followed by an exponential fall off, which continues past the distal edge of the target, which is at approximately 15 cm depth in the diagram. The x-ray beam has an entrance (skin) dose set to match that of the proton beam. With normalization (e.g., scaling) at 15 cm depth, the dose due to x-rays is at 40% of the dose provided by proton beam, while the x-ray beam has a peak dose of greater than 95% ("near" 100%) at approximately 3 cm depth. If the x-ray data is renormalized to achieve 100% dose at 15 cm, the peak dose at approximately 3 cm depth would be approximately 240%, in a location where dose is not desired (e.g., prior to the target). Therefore, with x-rays, a considerable amount of dose is delivered prior to the target and an appreciable amount of dose is delivered past the target.

The mono-energetic carbon beam shows a plateau region at the entrance dose that is lower than the proton beam. The carbon beam has a sharper Bragg Peak that falls more precipitously than the proton beam, but the carbon beam has a tail (e.g., known as a "spallation tail", where some of the Carbon nuclei shatter into Helium ions) that has approximately 10% additional dose, or less, past the desired target by several centimeters. The carbon ion beam has an undesired entrance and skin dose compared to the proton beam, but the carbon ion beam has a non-trivial dose delivered past the target.

Figure 5:
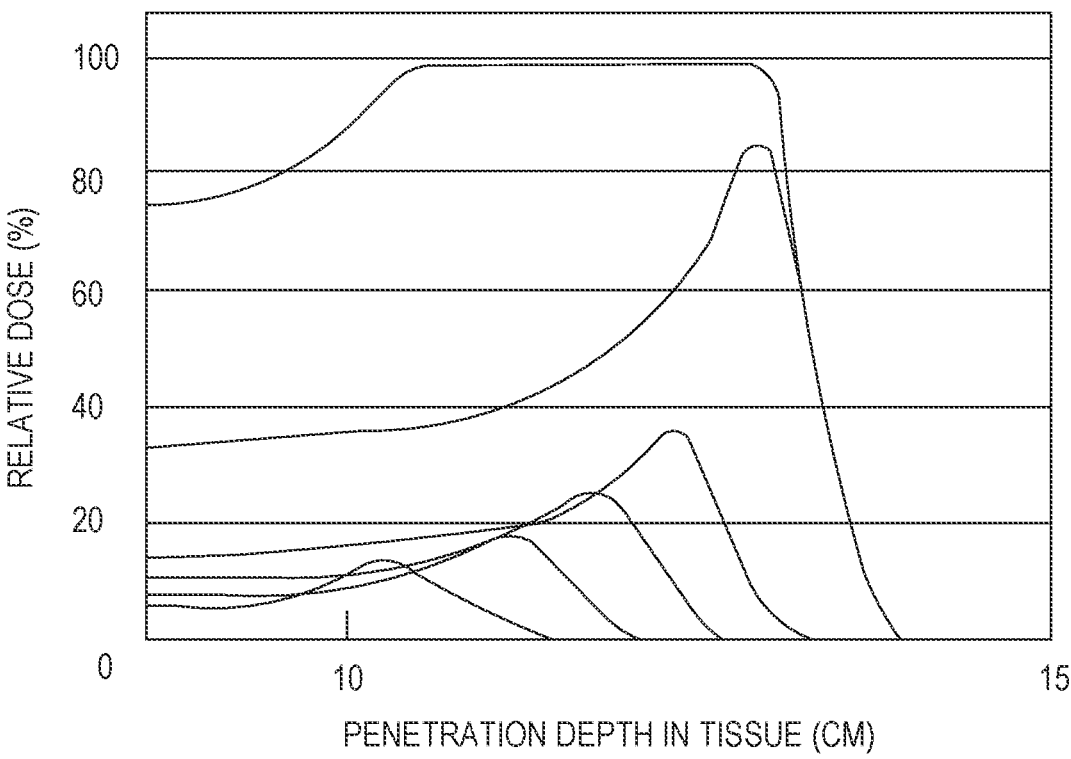
FIG. 5 illustrates generally a spread-out Bragg Peak, in accordance with an embodiment.

FIG. 5 provides an illustration of a spread-out Bragg peak (SOBP). The SOBP displays a relative depth dose curve for the combination of a set of proton beams of various initial energies each of which has had some spread in energy (e.g., variable absorption of energy in tissue). The desired result of having a uniform dose for a target of a particular thickness. As shown, the target is shown with a proximal depth of approximately 10 cm, a distal depth of approximately 13 cm, and a target thickness of approximately 3 cm, Within the target, the dose is quite uniform (with an average normalized at 100%). The diagram does not start at 0 cm depth and is not explicitly showing the entrance (skin) dose, but the nature of the entrance region of proton beams is a relatively flat depth dose curve. Typically, the entrance (skin) dose will be approximately 70% of the target dose (e.g., shown at the far right edge of the x-axis). A SOBP may be obtained using a variety of approaches, including using a scattered proton beam with modulation of the energy (variable absorption) utilizing a variety of devices (e.g., a static ridge filter or a dynamic range modulation wheel), or by selection of a number of mono-energetic proton beams that do not undergo scatter.

Figure 6:
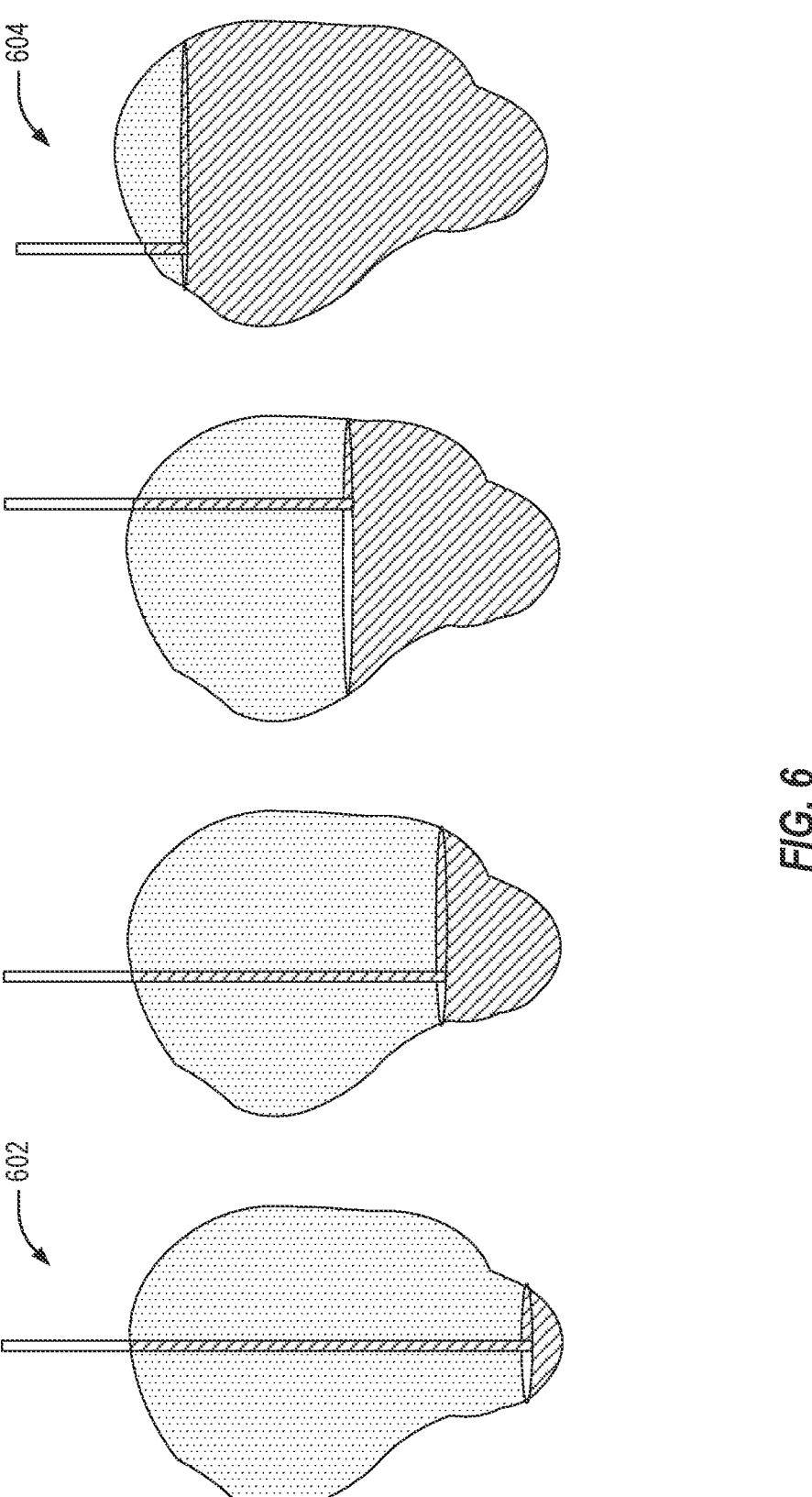
FIG. 6 illustrates generally pencil beam scanning of an irregular shape volume from distal edge to proximal edge, in accordance with an embodiment.

FIG. 6 provides an illustration of a Pencil Beam Scanning of an irregular shape volume from a distal edge (e.g., bottom) to a proximal (e.g., top) edge. As shown, the irregular shaped tumor volume is irradiated layers of protons. For example, a first time snapshot 602 shows a first layer of protons being delivered, and a later time snapshot 604 shows that most of the layers have been delivered. Each layer has its own cross-sectional area to which the protons having the same energy are delivered. The total radiation dose is provided as a layer-by-layer set of beamlets. Each layer of may have different energies. The most common means of specifying and delivering the set of beamlets to the cross-sectional area is to define and deliver beamlets having a constant diameter ("spot size") to a selection of grid points on each layer. While the majority of the dose from the beamlet is delivered to the targeted layer, a significant amount of dose is delivered along the path to the targeted layer. The dose to proximal layers from beamlets defined for distal layers is accounted for in the specification of the beamlets defined for the proximal layers. The ability to individually specify the number of particles (e.g., the meter-set) for a given beamlet ensures that each part of the volume being irradiate receives the desired dose.

Figure 7:
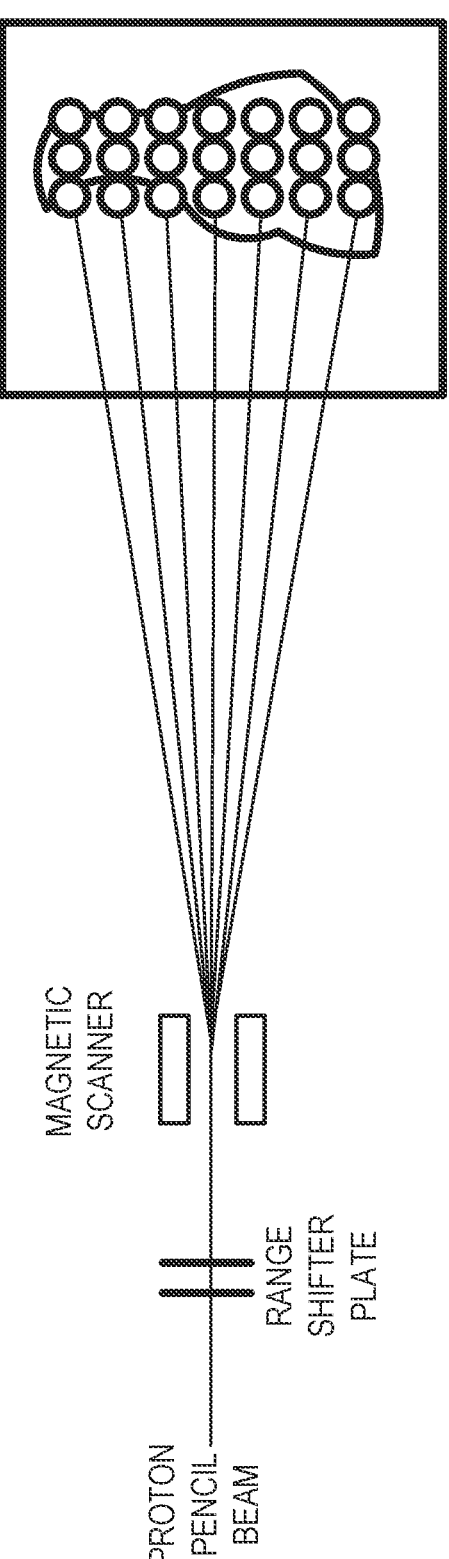
FIG. 7 illustrates generally a diagram of an active scanning proton beam delivery system, in accordance with an embodiment.

FIG. 7 provides an illustration of a diagrammatic representation of a typical active scanning proton beam delivery system. As shown, a single layer of a pencil beam scan is being delivered, with a grid of spots depicted on a patient in conjunction with a contour of the cross-sectional area to which particles are to be delivered. An incoming mono-energetic proton beamlet has a specified amount of its energy absorbed by the Range Shifter (e.g., in FIG. 7 it is a Range Shifter plate), resulting in a beamlet with the desired energy to achieve a certain depth for the Bragg Peak in the patient to treat the specified layer. A magnetic scanner, which has the ability to deflect the particles in both a vertical and a horizontal direction. The strength of the magnetic fields may be adjusted to control the deflection in the direction perpendicular to the magnetic field and the incoming beamlet. The rate at which the magnetic field strengths may be adjusted determines the rate at which the scanning may take place. For example, the intensity of the proton beamlet in combination with the scanning rate determines how much dose may be delivered to a specific area (e.g., in FIG. 7, a "spot") in a particular amount of time (e.g., particles/unit area). In theory, the magnetic field strengths may be adjusted independently of each other (in a fashion similar to the children's toy "Etch a Sketch®", provided by Spin Master™, Toronto, Canada; with the pencil beamlet intensity being a variable not available in the children's toy). The most common scheme for scanning is to scan in one direction quickly and to scan in the perpendicular direction more slowly in a raster fashion, similar to how early televisions were controlled (e.g., Cathode Ray Tube (CRT), which use electrons instead of protons), but arbitrary patterns may be scanned (similar to the previously mentioned toy). Delivery of distinct spots is achieved by incrementing the scanning magnetic field strength and throttling the pencil beam intensity between increments.

Figure 8:
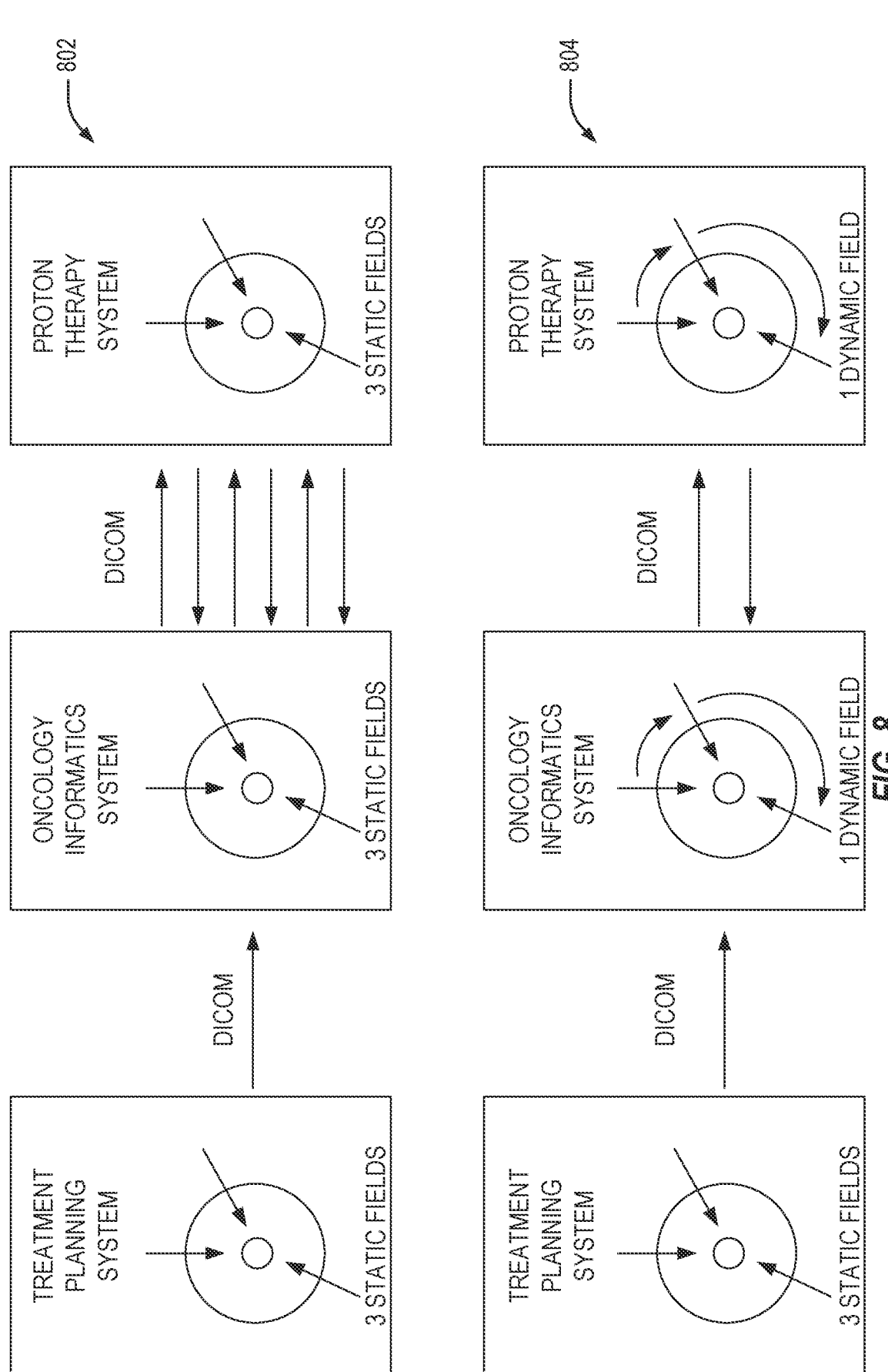
FIG. 8 illustrates a schematic diagram for composite field sequencing for proton therapy, in accordance with an embodiment.

FIG. 8 illustrates a schematic diagram for composite field sequencing for proton therapy, in accordance with an embodiment. The schematic drawing includes a first process flow 802 and a second process flow 804. The first process flow 802 illustrates a typical communication path for planning a proton therapy treatment. The second process flow 804 illustrates an improved communication path for planning a proton therapy treatment.

The first process flow 802 and the second process flow 804 may use a treatment planning system (TPS), an oncology informatics system (OIS), and a proton therapy system (PTS). Communication may flow between the TPS and the OIS and between the OIS and the PTS. The TPS may be used to generate a treatment plan, for example including planning a set of static fields for delivering proton therapy to a target of a patient. The PTS may be used to deliver the proton therapy to the target of the patient according to the treatment plan.

In the first process flow 802, the OIS sends a set of Digital Imaging and Communications in Medicine (DICOM) data files (e.g., each including an image corresponding to each static field of the treatment plan to the PTS). This process is time consuming, with each DICOM data file taking approximately a minute to complete. Thus, for the three fields of the first process flow 802, the communication between the OIS and the PTS takes around three minutes. The OIS may send a field DICOM data file, wait for the PTS to deliver the field dose, receive an indication from the PTS (e.g., a DICOM data file including information about of the delivered dose, an indication that the dose has been delivered, etc.), and then send a second field DICOM data file. Thus, the treatment is delayed for the various back and forth that must occur between the OIS and the PTS.

In the second process flow 804, the OIS creates a single dynamic field from the three static fields planned by the TPS. The OIS may generate a single DICOM data file for the single dynamic field. The single DICOM data file may be transmitted from the OIS to the PTS. The PTS may use the single dynamic field to deliver the planned doses (e.g., using static steps corresponding to the static field, which are represented in the single dynamic field). The PTS may send an indication to the OIS (e.g., a DICOM data file including information corresponding to the delivered dose, an indication that the dose has been delivered, etc.) when the delivery is complete. The use of the single dynamic field and the single DICOM data file reduces the communication between the OIS and the PTS to a single send and receive pair. The second process flow 804 may be scaled, such as by increasing the number of static fields planned at the TPS (e.g., to five, ten, fifteen, sixteen, twenty, etc. static fields), while maintaining a single dynamic field that is transmitted in a single DICOM data file to the TPS.

The technical problem of transmission time when using static fields each with corresponding images and data files (e.g., in the first process flow 802) is that a clinic may be limited to a set number of beams per patient due to the limit on a number of patients per day that may be scheduled due to wait time for data transmission. The first process flow 802 creates a potential limit when optimizing clinical efficiency and patient results. The second process flow 804 allows for optimizing patient results without consideration of clinical efficiency.

Operation of treatment machines, planning workflow interfaces, or communication time may be improved by using the second process flow 804, and accordingly patient treatments and outcomes may be improved. For example, beam arrangements may be standardized across a patient or across a set of patients. Instead of considering optimizing a few beams as in the first process flow 802, a larger number of beams may be used as a default (e.g., 16-beam geometry). This not only increases the number of beam geometries that may be used, but also allows for easier optimization due to the overlap of the beam delivery on a target of a patient. For example, with three static beams, configuration of the fields may need to be done manually for optimization. With a default beam geometry having more fields, the optimization may be automated or reused from a previous patient or treatment.

When proton beam therapy (PBT) treatment plans are exported from a treatment planning system for clinical delivery, individual beams are exported and used for treatment delivery on the appropriate delivery system. During treatment delivery, treatment plans may be sent to a delivery device from an oncology information system on a daily basis. When multiple beams are present in a plan, the delivery device records each field after it is treated, extending the treatment session length by up to or more than a minute per beam, during which the user must wait for data transfer to occur. However, with a large number of beams, users may be deterred by extended treatment delivery times, caused by beam-level data transfer.

The second process flow 804 allows a user to automate the placement of multiple beams (e.g., for static-arc purposes) or change the export method of the DICOM data file (e.g., that includes an image, delivery instructions, etc.) so that many beams are combined into a single beam. This removes processing time, network transmission time, data storage requirements, the wait time a user faces during treatment delivery, etc.

The second process flow 804 may consolidate all beams from the TPS into a single beam on export from the TPS to the OIS or the PTS (e.g., a proton delivery device). Multiple proton beam therapy (PBT) beams may be expressed as a single control point sequence in the DICOM standard file format, in some examples. For example, multiple static beams may be combined into a single beam that automatically moves between the delivery angles of the individual source beams. During treatment delivery, a user may only transfer and record data for a single beam, significantly reducing time spent waiting for these actions to occur when multiple beams are used. Beams may be consolidated on export from the TPS (e.g., not before they are about to be exported, such as not individually exported), which may allow for avoiding impeding on plan quality or treatment planning system functionality.

Figure 9:
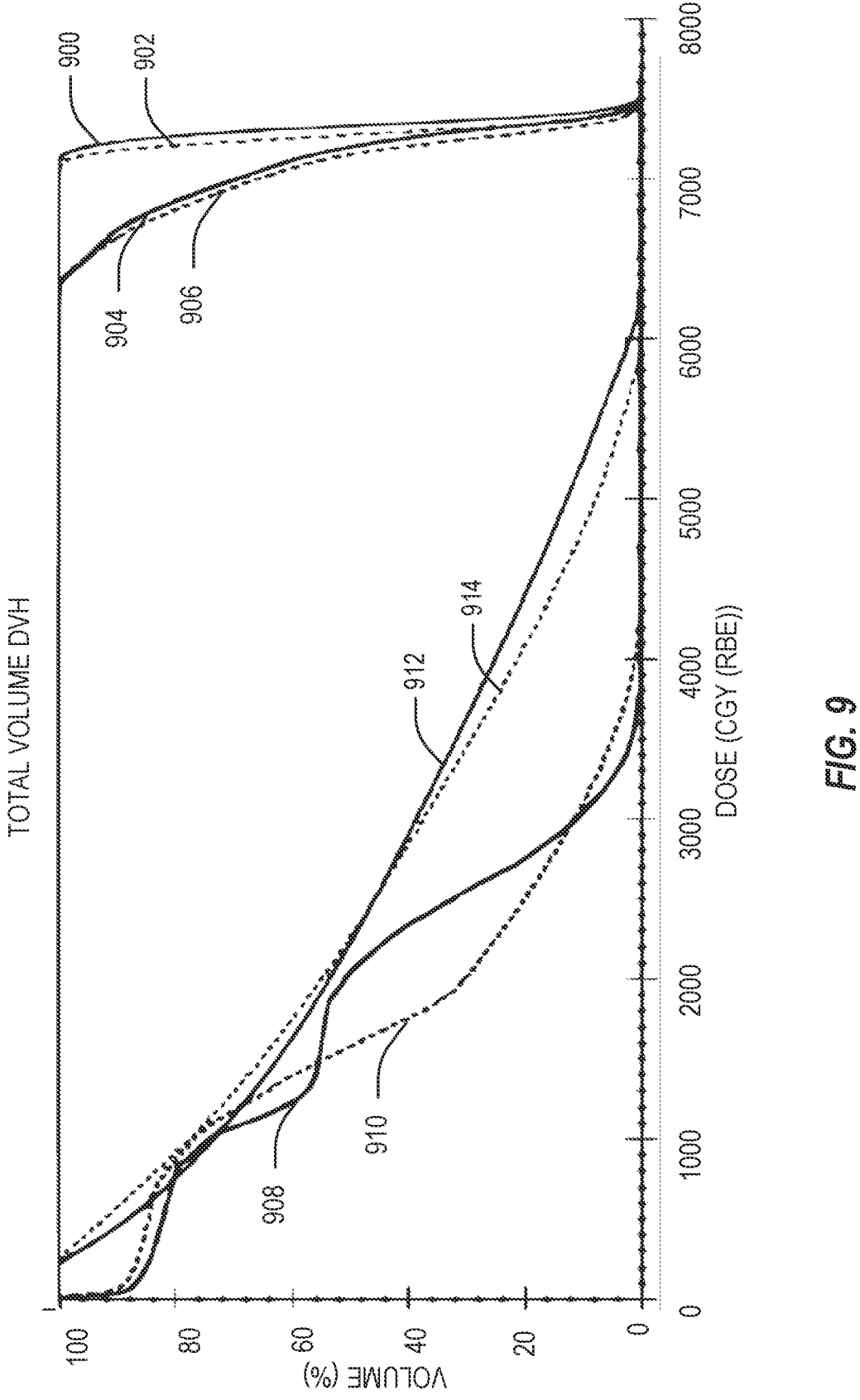
FIG. 9 illustrates a graph showing dose comparisons between proton therapy plans, in accordance with an embodiment.

FIG. 9 illustrates a graph showing dose comparisons between proton therapy plans, in accordance with an embodiment. The graph includes sets of lines corresponding to a 16-field plan (e.g., as delivered via a single dynamic field provided via a single data file) and a 3-field plan (e.g., as delivered via three separate fields from three separate data files). There are four different sets of lines, each of which corresponds to a different target or organ at risk. For example, lines 900, 902, 904, and 906 correspond to doses applied to a target. Of these lines, 900 and 904 correspond to 16-field plans and lines 902 and 906 correspond to 3-field plans. The dose given to each of the two targets is similar or higher for each of the two 16-field plans than for respective 3-field plans.

Similarly, lines 908, 910, 912, and 914 correspond to dose delivered to an organ at risk. For lines 908 and 910, the organ at risk may include a spinal cord and for lines 912 and 914, the organ at risk may include a right parotid. The lines 908 and 912 correspond to 16-field plans and lines 910 and 914 correspond to 3-field plans. The doses delivered to each of the organs at risk is comparable for respective field plans.

Figure 10:
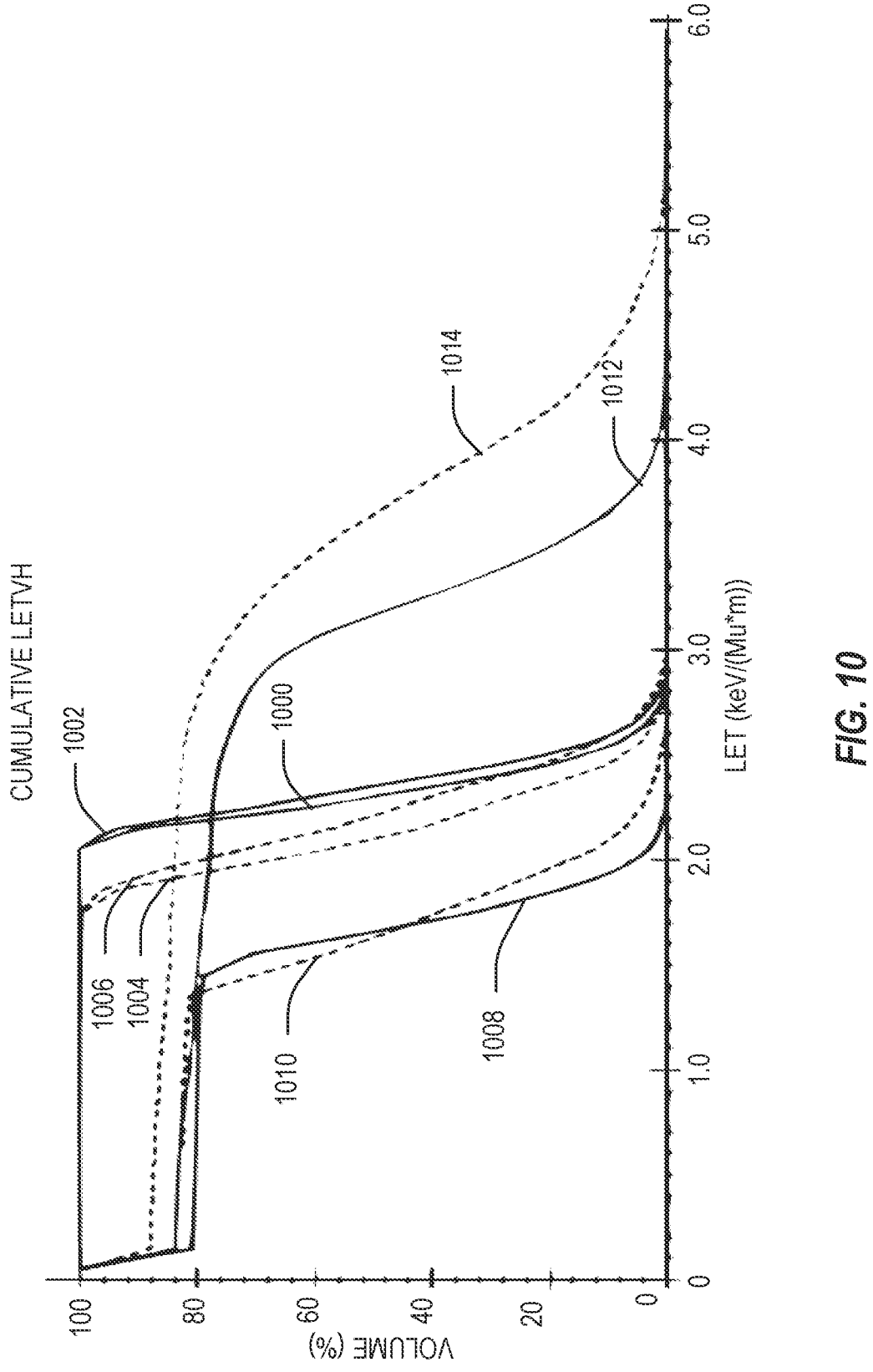
FIG. 10 illustrates a graph showing linear energy transfer comparisons between proton therapy plans, in accordance with an embodiment.

FIG. 10 illustrates a graph showing linear energy transfer (LET) comparisons between proton therapy plans, in accordance with an embodiment. The graph includes sets of lines corresponding to a 16-field plan (e.g., as delivered via a single dynamic field provided via a single data file) and a 3-field plan (e.g., as delivered via three separate fields from three separate data files). There are four different sets of lines, each of which corresponds to a different target or organ at risk. For example, lines 1000, 1002, 1004, and 1006 correspond to LET at a target. Of these lines, 1000 and 1004 correspond to 16-field plans and lines 1002 and 1006 correspond to 3-field plans. The LET at each of the two targets is similar or higher for each of the two 16-field plans than for respective 3-field plans.

Similarly, lines 1008, 1010, 1012, and 1014 correspond to LET at an organ at risk. For lines 1008 and 1010, the organ at risk may include a spinal cord and for lines 1012 and 1014, the organ at risk may include a right parotid. The lines 1008 and 1012 correspond to 16-field plans and lines 1010 and 1014 correspond to 3-field plans. The LET at the spinal cord organ at risk is comparable for respective field plans and the LET at the right parotid is lower for the 16-field plan than the 3-field plan.

Linear Energy Transfer (LET) gains (e.g., at a target) from Composite Field Sequencing (CFS) may occur based on using a static arc plan, which simulates a proton arc by using a single dynamic field with static steps. More fields may be used in the dynamic field, improving LET performance. The LET may be lower at an organ at risk using the dynamic field, as shown in FIG. 10. When a proton dose is delivered from multiple angles instead of the limited number available for static field delivery (e.g., typically three), LET distributions may be improved, which improve tumor control and reduce toxicity to critical organs.

One of the reasons why the LET changes with a different field distribution is based on radiological differences in proton therapy compared to photon therapy. In proton therapy, a Bragg peak models the energy distribution given by the proton, which includes asymmetrical energy delivery along a beam path (e.g., see FIGS. 4-5). Because the proton therapy delivers energy along a Bragg peak, the LET may be used to estimate the dose given to a patient. In some examples, a target or organ at risk may have a same dose distribution for two given beams, but when the two given beams have two different beam geometries, the result is differing LETs. The performance improvement for energy distribution corresponds to an increase in number of fields.

Without the systems and techniques described herein, using more than a few fields (e.g., three) may be impossible or impractical. For example, each data file transfer may take up to or over a minute, and each field may have an associated image and data file. The systems and techniques described herein reduce the transfer time to that needed to send a single data file, regardless of how many fields are in a plan.

FIG. 11 illustrates a flowchart showing a technique 1100 for composite field sequencing for proton therapy, in accordance with an embodiment.

The technique 1100 includes an operation 1102 to generate a proton therapy plan including a plurality of static fields. Operation 1102 may be performed using a treatment planning system. In some examples, the plurality of static fields may include 5, 10, 15, 16, 20, etc. static fields.

The technique 1100 includes an operation 1104 to process the plurality of static fields to create a single data file of a single dynamic field representing the plurality of static fields. Operation 1104 may be performed by an oncology informatics system or the treatment planning system, for example in response to receiving the proton therapy plan (e.g., from the treatment planning system) at the oncology informatics system or in response to generating the proton therapy plan. The single dynamic field may be generated based on a planned dosage to be delivered by the plurality of static fields to a patient. When considering the planned dosage, a linear energy transfer to a target may be greater for the single dynamic field than it would be for a set of static fields delivered separately where each of the single dynamic field and the set of static fields delivered the same planned dosage. In some examples, an actual biological damage delivered to a target may be greater for the single dynamic field than for a set of static fields with each relying on the same planned dosage. Operation 1104 may include processing the plurality of static fields in response to a user selection on a user interface to export the single dynamic field.

The technique 1100 includes an operation 1106 to send the single data file (e.g., in a data file) to a proton therapy system for delivery of the single dynamic field. The operations 1104 and 1106 may be performed more quickly than processing the plurality of static fields to generate a respective plurality of data files and sending the respective plurality of data files (e.g., separately) would take to complete. The single data file may include a single DICOM data file.

The technique 1100 includes an optional operation 1108 to receive (e.g., from the proton therapy system, at the oncology informatics system) a response indicating information related to a dose delivered to a patient by the single dynamic field. In an example, the response information may include a single Digital Imaging and Communications in Medicine (DICOM) response data file. The proton therapy system may be configured to deliver the single dynamic field in static steps with each step of the static steps corresponding to one of the plurality of static fields.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

Example 1 is a method for composite field sequencing for proton therapy, the method comprising: generating a proton therapy plan in a treatment planning system, the proton therapy plan including a plurality of static fields; in response to generating the proton therapy plan, processing the plurality of static fields to create a single data file of a single dynamic field representing the plurality of static fields based on a planned dosage to be delivered by the plurality of static fields to a patient; sending the single data tile to a proton therapy system for delivery of the single dynamic field; and receiving a response indicating information related to a dose delivered to a patient by the single dynamic field.

In Example 2, the subject matter of Example 1 includes, wherein the single data file is a single Digital Imaging and Communications in Medicine (DICOM) data file.

In Example 3, the subject matter of Examples 1-2 includes, wherein processing the plurality of static fields to create the single data file and sending the single data file is performed in less time than a time calculated to process the plurality of static fields to generate a respective plurality of data files and sending the respective plurality of data files.

In Example 4, the subject matter of Examples 1-3 includes, wherein for the planned dosage, a linear energy transfer to a target is greater for the single dynamic field than a linear energy transfer calculated for a set of static fields, each delivering the same planned dosage.

In Example 5, the subject matter of Examples 1-4 includes, wherein for the planned dosage, an actual dosage delivered to a target is greater for the single dynamic field than an actual dosage calculated for a set of static fields.

In Example 6, the subject matter of Examples 1-5 includes, wherein for the planned dosage, a linear energy transfer to a non-target area is lower for the single dynamic field than a linear energy transfer calculated for a set of static fields, each delivering the same planned dosage.

In Example 7, the subject matter of Examples 1-6 includes, wherein for the planned dosage, an actual dosage delivered to a non-target area is lower for the single dynamic field than an actual dosage calculated for a set of static fields.

In Example 8, the subject matter of Examples 1-7 includes, wherein the plurality of static fields includes at least sixteen static fields.

In Example 9, the subject matter of Examples 1-8 includes, wherein the proton therapy system is configured to deliver the single dynamic field in static steps with each step of the static steps corresponding to one of the plurality of static fields.

In Example 10, the subject matter of Examples 1-9 includes, wherein processing the plurality of static fields to create the single data file of the single dynamic field includes processing the plurality of static fields in response to a user selection on a user interface to export the single dynamic field.

Example 11 is at least one machine-readable medium including instructions for composite field sequencing for proton therapy, which when executed by processing circuitry, causes the processing circuitry to perform operations to: generate a proton therapy plan in a treatment planning system, the proton therapy plan including a plurality of static fields; in response to generating the proton therapy plan, process the plurality of static fields to create a single data file of a single dynamic field representing the plurality of static fields based on a planned dosage to be delivered by the plurality of static fields to a patient; send the single data file to a proton therapy system for delivery of the single dynamic field; and receive a response indicating information related to a dose delivered to a patient by the single dynamic field.

In Example 12, the subject matter of Example 11 includes, wherein the single data file is a single Digital Imaging and Communications in Medicine (DICOM) data file.

In Example 13, the subject matter of Examples 11-12 includes, wherein the operations to process the plurality of static fields to create the single data file and send the single data file occur in less time than a time calculated to perform operations to process the plurality of static fields to generate a respective plurality of data files and send the respective plurality of data files.

In Example 14, the subject matter of Examples 11-13 includes, wherein for the planned dosage, a linear energy transfer to a target is greater for the single dynamic field than a linear energy transfer calculated for a set of static fields, each delivering the same planned dosage.

In Example 15, the subject matter of Examples 11-14 includes, wherein for the planned dosage, an actual dosage delivered to a target is greater for the single dynamic field than an actual dosage calculated for a set of static fields.

In Example 16, the subject matter of Examples 11-15 includes, wherein for the planned dosage, a linear energy transfer to a non-target area is lower for the single dynamic field than a linear energy transfer calculated for a set of static fields, each delivering the same planned dosage.

In Example 17, the subject matter of Examples 11-16 includes, wherein for the planned dosage, an actual dosage delivered to a non-target area is lower for the single dynamic field than an actual dosage calculated for a set of static fields.

In Example 18, the subject matter of Examples 11-17 includes, wherein the plurality of static fields includes at least sixteen static fields.

In Example 19, the subject matter of Examples 11-18 includes, operations to control the proton therapy system to deliver the single dynamic field in static steps with each step of the static steps corresponding to one of the plurality of static fields.

In Example 20, the subject matter of Examples 11-19 includes, wherein the operation to process the plurality of static fields to create the single data file of the single dynamic field occurs in response to a user selection on a user interface to export the single dynamic field.

Example 21 is at least one machine-readable medium including instructions that, when executed by processing circuitry, cause the processing circuitry to perform operations to implement ofany of Examples 1-20.

Example 22 is an apparatus comprising means to implement of any of Examples 1-20.

Example 23 is a system to implement of any of Examples 1-20.

Example 24 is a method to implement of any of Examples 1-20.

What is claimed is:

1. A method for composite field sequencing for proton therapy, the method comprising:
   generating a proton therapy plan in a treatment planning system, the proton therapy plan including a plurality of static fields, wherein each of the plurality of static fields defines a configuration of an individual proton therapy beam to be delivered with pencil beam scanning from a proton therapy system;
   in response to generating the proton therapy plan, processing the plurality of static fields to create a single data file of a single dynamic field including a plurality of static steps,
   wherein each of the plurality of static steps corresponds with a respective static field of the plurality of static fields, the correspondence being determined based on a planned dosage to be delivered by the plurality of static fields to a patient with the proton therapy plan, and
   wherein processing the plurality of static fields includes combining a plurality of source beams, each corresponding with an individual static step, into a single beam that automatically moves between different delivery angles;
   sending the single data file to the proton therapy system for delivery of the single dynamic field; and
   receiving a response indicating information related to a dose delivered to a patient by the single dynamic field.

2. The method of claim 1, wherein the single data file is a single Digital Imaging and Communications in Medicine (DICOM) data file.

3. The method of claim 1, wherein processing the plurality of static fields to create the single data file and sending the single data file is performed in less time than a time calculated to process the plurality of static fields to generate a respective plurality of data files and sending the respective plurality of data files.

4. The method of claim 1, wherein for the planned dosage, a linear energy transfer to a target is greater for the single dynamic field than a linear energy transfer calculated for a set of static fields, each delivering the same planned dosage.

5. The method of claim 1, wherein for the planned dosage, an actual dosage delivered to a target is greater for the single dynamic field than an actual dosage calculated for a set of static fields.

6. The method of claim 1, wherein for the planned dosage, a linear energy transfer to a non-target area is lower for the single dynamic field than a linear energy transfer calculated for a set of static fields, each delivering the same planned dosage.

7. The method of claim 1, wherein for the planned dosage, an actual dosage delivered to a non-target area is lower for the single dynamic field than an actual dosage calculated for a set of static fields.

8. The method of claim 1, wherein the plurality of static fields includes at least sixteen static fields.

9. The method of claim 1, wherein the proton therapy system is configured to deliver the single dynamic field in static steps with each step of the static steps corresponding to one of the plurality of static fields.

10. The method of claim 1, wherein processing the plurality of static fields to create the single data file of the single dynamic field includes processing the plurality of static fields in response to a user selection on a user interface to export the single dynamic field.

11. At least one non-transitory machine-readable medium including instructions for composite field sequencing for proton therapy, which when executed by processing circuitry, causes the processing circuitry to perform operations to:

generate a proton therapy plan in a treatment planning system, the proton therapy plan including a plurality of static fields, wherein each of the plurality of static fields defines a configuration of an individual proton therapy beam to be delivered with pencil beam scanning from a proton therapy system;

in response to generating the proton therapy plan, process the plurality of static fields to create a single data file of a single dynamic field including a plurality of static steps, wherein each of the plurality of static steps corresponds with a respective static field of the plurality of static fields, the correspondence being determined based on a planned dosage to be delivered by the plurality of static fields to a patient with the proton therapy plan, and wherein processing the plurality of static fields includes combining a plurality of source beams, each corresponding with an individual static step, into a single beam that automatically moves between different delivery angles;

send the single data file to the proton therapy system for delivery of the single dynamic field; and receive a response indicating information related to a dose delivered to a patient by the single dynamic field.

12. The at least one machine-readable medium of claim 11, wherein the single data file is a single Digital Imaging and Communications in Medicine (DICOM) data file.

13. The at least one machine-readable medium of claim 11, wherein the operations to process the plurality of static fields to create the single data file and send the single data file occur in less time than a time calculated to perform operations to process the plurality of static fields to generate a respective plurality of data files and send the respective plurality of data files.

14. The at least one machine-readable medium of claim 11, wherein for the planned dosage, a linear energy transfer to a target is greater for the single dynamic field than a linear energy transfer calculated for a set of static fields, each delivering the same planned dosage.

15. The at least one machine-readable medium of claim 11, wherein for the planned dosage, an actual dosage delivered to a target is greater for the single dynamic field than an actual dosage calculated for a set of static fields.

16. The at least one machine-readable medium of claim 11, wherein for the planned dosage, a linear energy transfer to a non-target area is lower for the single dynamic field than a linear energy transfer calculated for a set of static fields, each delivering the same planned dosage.

17. The at least one machine-readable medium of claim 11, wherein for the planned dosage, an actual dosage delivered to a non-target area is lower for the single dynamic field than an actual dosage calculated for a set of static fields.

18. The at least one machine-readable medium of claim 11, wherein the plurality of static fields includes at least sixteen static fields.

19. The at least one machine-readable medium of claim 11, further comprising operations to control the proton therapy system to deliver the single dynamic field in static steps with each step of the static steps corresponding to one of the plurality of static fields.

20. The at least one machine-readable medium of claim 11, wherein the operation to process the plurality of static fields to create the single data file of the single dynamic field occurs in response to a user selection on a user interface to export the single dynamic field.

21. The at least one machine-readable medium of claim 11, wherein the single dynamic field including the plurality of static steps is established based on automating a placement of multiple beams included in the dose delivered to the patient.

22. The at least one machine-readable medium of claim 21, wherein the single dynamic field including the plurality of static steps each corresponding with a respective static field is received by the proton therapy system to deliver a plurality of proton beam therapy (PBT) beams expressed as a single control point sequence.

23. The method of claim 1, wherein the single dynamic field including the plurality of static steps is established based on automating a placement of multiple beams included in the dose delivered to the patient.

24. The method of claim 23, comprising, based on the single dynamic field including the plurality of static steps each corresponding with a respective static field, delivering a plurality of proton beam therapy (PBT) beams expressed as a single control point sequence.

* * * * *